United States Patent
Jiang et al.

(10) Patent No.: US 6,544,781 B1
(45) Date of Patent: Apr. 8, 2003

(54) NON-DEFECTIVE EPSTEIN-BARR VIRAL VECTOR

(75) Inventors: Xiaoqun Jiang, Quincy, MA (US); E. Antonio Chiocca, Wakefield, MA (US); Elliott Kieff, Brookline, MA (US); Fred Wang, Chestnut Hill, MA (US); Fred Hochberg, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/617,800

(22) Filed: Jul. 17, 2000

Related U.S. Application Data

(60) Provisional application No. 60/144,021, filed on Jul. 15, 1999.
(51) Int. Cl.$^7$ .................. C12N 15/00; C12N 15/09; C12N 15/63; C12N 15/70; C12N 15/74
(52) U.S. Cl. .............. 435/320.1; 435/325; 435/455; 514/44
(58) Field of Search ................. 435/320.1, 325, 435/455; 514/44

(56) References Cited

U.S. PATENT DOCUMENTS

| | | | |
|---|---|---|---|
| 5,529,774 A | 6/1996 | Barba et al. | 424/93.21 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/44 |
| 5,688,773 A | 11/1997 | Chiocca et al. | 514/44 |
| 5,691,177 A | 11/1997 | Guber et al. | 435/172.3 |
| 5,763,217 A | 6/1998 | Cynader et al. | 435/69.1 |

FOREIGN PATENT DOCUMENTS

| | | |
|---|---|---|
| WO | WO 98/21345 | 5/1998 |

OTHER PUBLICATIONS

Anderson, W.F., "Human gene therapy," *Nature* 392:25–30, Nature Publishing Group (1998).

Rogers, R.P. et al., "Killing Epstein–Barr Virus–Positive B Lymphocytes by Gene Therapy: Comparing the Efficacy of Cytosine Deaminase and Herpes Simplex Virus Thymidine Kinase," *Hum. Gene Ther.* 7:2235–2245, Mary Ann Liebert, Inc. (1996).

Verma, I.M. and Somia, N., "Gene therapy—promises, problems, and prospects," *Nature* 389:239–242, Nature Publishing Group (1997).

Aghi, M. et al., "Prodrug activation enzymes in cancer gene therapy," *J. Gene Med.* 2:148–164 (2000).

Banerjee, S. et al., "Therapeutic gene delivery in human B–lymphoblastoid cells by engineered non–transforming infectious Epstein–Barr virus," *Nature Med.* 1:1303–1308 (1995).

Boviatsis, E.J. et al., "Long–Term Survival of Rats Harboring Brain Neoplasms Treated with Ganciclovir and a Herpes Simplex Virus Vector that Retains an Intact Thymidine Kinase Gene," *Cancer Res.* 54:5475–5751 (1994).

Cachianes, G. et al., "Epstein–Barr Virus–Derived Vectors for Transient and Stable Expression of Recombinant Proteins," *BioTechniques* 15:255–259 (1993).

Chase, M. et al., "An oncolytic viral mutant that delivers the CYP2B1 transgene and augments cyclophosphamide chemotherapy," *Nature Biotechnol.* 16:444–448 (1998).

Chen, L. and D.J. Waxman, "Intratumoral Activation and Enhanced Chemotherapeutic Effect of Oxazaphosphorines following Cytochrome P–450 Gene Transfer: Development of a Combined Chemotherapy/Cancer Gene Therapy Strategy," *Cancer Res.* 55:581–589 (1995).

Cheung, A. and E. Kieff, "Long Internal Direct Repeat in Epstein–Barr Virus DNA," *J. Virology* 44:286–294 (1982).

Delecluse, H.–J. et al., "Propagation and recovery of intact, infectious Epstein–Barr virus from prokaryotic to human cells," *Proc. Natl. Acad. Sci. USA* 95:8245–8250 (Jul. 1998).

Ezzeddine, Z.D. et al., "Selective Killing of Glioma Cells in Culture and in Vivo by Retrovirus Transfer of the Herpes Simplex Virus Thymidine Kinase gene," *New Biol.* 3:608–614 (1991).

Fraefel, C. et al., "Helper Virus–Free Transfer of Herpes Simplex Virus Type 1 Plasmid Vectors into Neural Cells," *J. Virology* 70:7190–7197 (1996).

Freeman, S.M. et al., "In Situ Use of Suicide Genes for Cancer Therapy," *Semin. Oncology* 23:31–45 (1996).

Glorioso, J.C. et al., "Herpes Simplex Virus as a Gene–Delivery Vector for the Central Nervous System," in *Viral Vectors, Gene Therapy and Neuroscience Applications*, Kaplitt, M.G. and A.D. Loewy, eds., Academic Press, San Diege, CA, pp. 1–23 (1995).

Jacoby, D.R. et al., "Hybrid vectors: a new generation of virus–based vectors designed to control the cellular fate of delivered genes," *Gene Ther.* 4:1281–1283 (1997).

Karle, P. et al., "Intratumoral Injection of Encapsulated Cells Producing an Oxazaphosphorine Activating Cytochrome P450 for Targeted Chemotherapy," in *Gene Therapy of Cancer*, Walden et al., eds., Plenum Press, NY, pp. 97–106 (1998).

(List continued on next page.)

Primary Examiner—Scott D. Priebe
Assistant Examiner—Peter Paras, Jr.
(74) Attorney, Agent, or Firm—Sterne, Kessler, Goldstein & Fox PLLC

(57) ABSTRACT

The present invention relates to a viral vector system derived from Epstein-Barr Virus (EBV), where the transgene is effectively inserted into the EBV major internal repeat region (IR1) without adverse affect on EBV latent or lytic function. The vector of the invention can target and stably transform B-lymphocyte cells, both in culture and in vivo.

4 Claims, 9 Drawing Sheets

OTHER PUBLICATIONS

Kenney, S. et al., "Gene Therapy Strategies for Treating Epstein–Barr Virus–Associated Lymphomas: Comparison of Two Different Epstein–Barr Virus–Based Vectors," *Human Gene Ther.* 9:1131–1141 (May 1998).

Lei, D.C. et al., "Episomal expression of wild–type CFTR corrects cAMP–dependent chloride transport in respiratory epithelial cells," *Gene Ther.* 3:427–436 (1996).

Luckow, V.A. et al., "Efficient Generation of Infectious Recombinant Baculoviruses by Site–Specific Transposon–Mediated Insertion of Foreign Genes into a Baculovirus Genome Propagated in *Escherichia coli*," *J. Virology* 67:4566–4579 (1993).

McGarry, T.J. et al., "Inhibition of heat shock protein synthesis by heat–inducible antisense RNA," *Proc. Natl. Acad. Sci. USA* 83:399–403 (1986).

Messerle, M. et al., "Cloning and mutagenesis of a herpesvirus genome as an infectious bacterial artificial chromosome," *Proc. Natl. Acad. Sci. USA* 94:14759–14763 (1997).

Mullen, C.A. et al., "Tumors Expressing the Cytosine Deaminase Suicide Gene Can Be Eliminated in Vivo with 5–Fluorocytosine and Induce Protective Immunity to Wild Type Tumor," *Cancer Res.* 54:1503–1506 (1994).

Nakanishi, M. et al., "Gene Introduction Into Animal Tissues," *Crit. Rev. Therapeut. Drug Carrier Systems* 12:263–310 (1995).

O'Connor, M. et al., "Construction of Large DNA Segments in *Escherichia coli*," *Science* 244:1307–1312 (1989).

Paillard, F., "Epstein–Barr Virus Vectors for the Treatment of Epstein–Barr Virus–Associated Cancers," *Human Gene Ther.* 9:1119–1120 (May 1998).

Robbins, P.D. et al., "Viral vectors for gene therapy," *TIBTECH* 16:35–40 (Jan. 1998).

Robertson, E.S. et al., "Epstein–Barr virus vectors for gene delivery to B lymphocytes," *Proc. Natl. Acad. Sci. USA* 93:11334–11340 (1996).

Saeki, Y. et al., "Herpes Simplex Virus Type 1 DNA Amplified as Bacterial Artificial Chromosome in *Escherichia coli*: Rescue of Replication–Competent Virus Progeny and Packaging of Amplicon Vectors," *Hum. Gene Ther.* 9:2787–2794 (Dec. 1998).

Sample, J. et al., "Nucleotide sequences of mRNAs encoding Epstein–Barr virus nuclear proteins: A probable transcriptional initiation site," *Proc. Natl. Acad. Sci. USA* 83:5096–5100 (1986).

Sclimenti, C.R. and M.P. Calos, "Epstein–Barr virus vectors for gene expression and transfer," *Curr. Opin. Biotechnol.* 9:476–479 (Oct. 1998).

Shimizu, N. et al., "Clonal Propagation of Epstein–Barr Virus (EBV) Recombinants in EBV–Negative Akata Cells," *J. Virology* 70:7260–7263 (1996).

Shizuya, H. et al., "Cloning and stable maintenance of 300–kilobase–pair fragments of human DNA in *Escherichia coli* using a F–factor–based vector," *Proc. Natl. Acad. Sci. USA* 89:8794–8797 (1992).

Speck, S.H. et al., "An Epstein–Barr virus transcript from a latently infected, growth–transformed B–cell line encodes a highly repetitive polypeptide," *Proc. Natl. Acad. Sci. USA* 83:9298–9302 (1986).

Weber, G.F. and D.J. Waxman, "Activation of the Anti–Cancer Drug Ifosphamide by Rat Liver Microsomal P450 Enzymes," *Biochem. Pharmacol.* 45:1685–1694 (1993).

Wei, M.X. et al., "Experimental Tumor Therapy in mice Using the Cyclophosphamide–Activating Cytochrome P450 2B1 Gene," *Hum. Gene Ther.* 5:969–978 (1994).

Wendelburg, B.J. and J.–M.H. Vos, "An enhanced EBNA1 variant with reduced IR3 domain for long–term episomal maintenance and transgene expression of oriP–based plasmids in human cells," *Gene Therapy* 5:1389–1399 (1998).

Westphal, E.M. et al., "A System for Shuttling 200–kb BAC/PAC Clones into Human Cells: Stable Extrachromosomal Persistence and Long–Term Ectopic Gene Activation," *Human Gene Therapy* 9:1863–1873 (Sep. 1998).

Wilson, J.M., "Vectors—shuttle vehicles for gene therapy," *Clin. Exp. Immunol.* 107(suppl):31–32 (1997).

Zhang, J. and S.J. Russell, "Vectors for cancer gene therapy," *Cancer & Metastasis Rev.* 15:385–401 (1996).

GFP expression of cells containing EBwgh

B95-8/EBwgh
with selection

PBL/EBwgh
without selection

IB4 superinfected with
EBwgh from PBL/EBwgh
with selection

FIG.9

PLASMID — GFP-Hyg$^r$ — ELECTROPORATION → B95-8 CELLS OR P3HRI CELLS

+

GENOME OF WILD-TYPE EBV

↓ HOMOLOGOUS RECOMBINATION IN W REGION

GENOME OF REC. EBV

POSITIVE/NEGATIVE SELECTION

MIXTURE

PBL CELLS OR 293 CELLS

SELECTION

PURE EBwgh

ACTIVATION

○ WILD EBV
⊘ RECOMBINANT EBV

NON-DEFECTIVE EPSTEIN-BARR VIRAL VECTOR

CROSS-REFERENCE TO RELATED APPLICATION

This application claims the benefit of U.S. Provisional Application No. 60/144,021, filed Jul. 15, 1999. The content of this application is relied upon and incorporated by reference in its entirety.

BACKGROUND OF THE INVENTION

1. Field of the Invention

The present invention relates to a viral vector construct derived from Epstein-Barr virus (EBV) that targets B-lymphocytes. The viral vector of the invention has a transgene inserted in the EBV major internal repeat region (IR1), for gene delivery and persistent gene expression in B-lymphocytes in vitro and in vivo.

2. Related Art

The terms "gene transfer" and "gene therapy" have been used to describe a variety of methods for delivering genetic material to a cell using viral or non-viral based vector systems. Substantial attention has been given to human gene therapy. The transfer of genetic material to a cell may one day become one of the most important forms of medicine. A variety of public and private institutions now participate in research and development related to the use of genetic material in therapeutic applications. Hundreds of human gene transfer protocols are being conducted at any given time with the approval of the Recombinant DNA Advisory Committee (RAC) and the National Institutes of Health (NIH). Most of these protocols focus on therapy, while others involve marking and non-therapeutic applications. The therapeutic protocols are primarily concerned with infectious diseases, monogenic diseases, and cancer. Gene-based therapies are now expanding into fields such as cardiovascular disease, autoimmune disease, and neurodegenerative disease. The availability of a safe and efficient gene delivery and expression system is essential to the success and efficacy of gene-based therapy.

One method of delivering a gene of interest to a target cell of interest is by using a viral-based vector. Techniques for the formation of vectors or virions are generally described in "Working Toward Human Gene Therapy," Chapter 28 in *Recombinant DNA, 2nd Ed.,* Watson, J. D. et al., eds., New York: Scientific American Books, pp. 567–581 (1992). An overview of viral vectors or virions that have been used in gene therapy can be found in Wilson, J. M., *Clin. Exp. Immunol.* 107(Suppl. 1):31–32 (1997), as well as Nakanishi, M., *Crit. Rev. Therapeu. Drug Carrier Systems* 12:263–310 (1995); Robbins, P. D., et al., *Trends Biotechnol.*16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Specific examples of viral vector systems that have been utilized include: retroviruses (Vile, R. G., supra; U.S. Pat. Nos. 5,741,486 and 5,763,242); adenoviruses (Brody, S. L., et al., *Ann. N.Y. Acad. Sci.* 716: 90–101 (1994); Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763,217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310 (1995)). Other viruses that can be used as vectors for gene delivery include poliovirus, papillomavirus, vaccinia virus, Epstein-Barr virus (EBV), and lentivirus, as well as hybrid or chimeric vectors incorporating favorable aspects of two or more viruses (Nakanishi, M., *Crit. Rev. Therapeu. Drug Carrier Systems* 12:263–310 (1995); Zhang, J., et al., *Cancer Metastasis Rev.* 15:385–401 (1996); Jacoby, D. R., et al., *Gene Therapy* 4:1281–1283 (1997); Robertson, E. S., et al., *Proc.Natl Acad.Sci.USA* 93:11334–11340(1996)). Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, and 5,601,818.

The viral vectors mentioned above each have advantages and disadvantages. For example, retroviruses have the ability to infect cells and have their genetic material integrated into the host cell with high efficiency. The development of a helper virus free packaging system for retrovirus vectors was a key innovation in the development of this vector system for human gene therapy. Retroviral helper virus free packaging systems generally employ the creation of a stable producer cell line that expresses a selected vector. The relatively small size of the retroviral genome (approximately 11 kb), and the ability to express viral genes without killing cells, allows for the production of a packaging cell line that synthesizes all the proteins required for viral assembly. Producer lines are made by introducing the retroviral vector into such a packaging cell line.

On a down side, however, numerous difficulties with retroviruses have been reported. For example, most retroviral vectors are not capable of gene transfer to postmitotic (nondividing) cells and thus are not applicable to the nervous system because most of the cells in the adult nervous system, especially neurons, are quiescent or postmitotic. In addition, outbreaks of wild-type virus from recombinant virus-producing cell lines have also been reported, with the vector itself causing a disease.

Difficulties have been noted with other viral vectors as well. Adenovirus vectors can only support limited long-term (2 months) gene expression, they appear to be gradually lost from neural cells, and moreover, they can cause both cytopathic effects and an immune response (Le Gal La Salle, G., et al., *Science* 259:988–990 (1993); Davidson et al., *Nat. Genet.* 3:219–223 (1993); Yang, Y., et al., *J. Virol.* 69:2004–2015 (1995)). Adeno-associated virus vectors cause minimal cytopathic effects and can support at least some gene expression for up to 4 months, but gene transfer is inefficient and these vectors can accept only about 4 kb of foreign DNA (Kaplitt, M. G., et al., *Nat. Genet.* 8:148–154 (1994)).

Vectors based on herpes simplex virus (HSV), and especially HSV-1, have shown promise as potent gene delivery vehicles for several reasons: the virus has a very large genome and thus can accommodate large amounts of foreign DNA (greater than 30 kb), the virus can persist long-term in cells, and can efficiently infect many different cell types, including post-mitotic neural cells (Breakefield, X. O., et al., "Herpes Simplex Virus Vectors for Tumor Therapy," in *The Internet Book of Gene Therapy: Cancer Gene Therapeutics,*

R. E. Sobol and K. J. Scanlon, eds., Appleton and Lange, Stamford, Conn., pp. 41–56 (1995); Glorioso, J. C., et al., "Herpes Simplex Virus as a Gene-Delivery Vector for the Central Nervous System," in Viral Vectors: *Gene Therapy and Neuroscience Applications*, M. G. Kaplitt and A. D. Loewy, eds., Academic Press, New York, pp. 1–23 (1995)).

Two types of HSV-1 vector systems are known: recombinant and amplicon. Recombinant HSV-1 vectors (Wolfe, J. H. et al., *Nat. Genet.* 1:379–384 (1992)) are created by inserting genes of interest directly into the 152 kb viral genome, thereby mutating one or more of the approximately 80 viral genes, and concomitantly reducing cytotoxicity. In contrast, HSV-1 amplicons are bacterial plasmids containing only about 1% of the 152 kb HSV-1 genome. They are packaged into HSV-1 particles (virions) using HSV-1 helper virus. HSV-1 amplicons contain: (i) a transgene cassette with a gene of interest; (ii) sequences that allow plasmid propagation in *E. coli,* such as the origin of DNA replication colE1 and the ampicillin resistance gene; and (iii) non-coding elements of the HSV-1 genome, in particular an origin of DNA replication (ori) and a DNA cleavage/packaging signal (pac), to support replication and subsequent packaging of the amplicon DNA into virions in the presence of helper functions (Spaete, R. R. and Frenkel, N., *Cell* 30:295–304 (1982)). HSV amplicon vectors are one of the most versatile, efficient, and least toxic, and have the largest transgene capacity of the currently available virus vectors. Because HSV-1 encodes many toxic functions, improvements on the amplicon system have been targeted at reducing the risk associated with the helper virus, or, more recently, using a helper virus-free packaging system (Fraefel, C., et al., *J. Virol.* 70:7190–7197 (1996); International Patent Publication WO 97/05263, published Feb. 13, 1997); Saeki, Y., et al., *Hum Gene Ther* 9:2787–2794 (1998)).

In addition to the alpha herpes viruses, such as HSV-1 and HSV-2, described above, viral vectors derived from the gamma herpes virus, Epstein-Barr virus (EBV), have also been used for gene delivery (Robertson, E. S.,et al., *Proc. Natl Acad.Sci. USA* 93:11334–11340(1996); Sclimenti, C. R., et al., *Current Opinion in Biotechnology* 9:476–479 (1998); Banerjee, S., et al., *Nature Med.*1:1303–1308 (December 1995); Cachianes, G., et al., *BioTechniques* 15:255–259 (1993); Kenney, S.,et al.,*Human Gene Therapy* 9:1131–1141 (May 1998)). For example, an EBV vector carrying the gene defective in cystic fibrosis provided gene expression for at least 2 months in transformed dividing human airway epithelial cells in culture (Lei, D. C., et al., *Gene Therapy* 3:427–436 (1996)).

EBV, which is also known as human herpes virus 4, is an about 180-kilobase, double-stranded DNA virus carried in an asymptomatic state by more than 90% of the worldwide adult human population, and is generally maintained as a circular episome in latently infected B cells. It is estimated that one B cell per milliliter of blood from a normal healthy person is infected with EBV.

EBV is highly B-lymphotropic, meaning it mainly infects B lymphocytes, and some epithelial cells. In initiation of latent infection in B lymphocytes, at least 9 viral latent genes are expressed. These viral proteins act in concert to alter B lymphocyte growth and enable the maintenance of the EBV genome as a multicopy episome in a state of latent infection. Each of the viral proteins expressed in latently infected cells, with the exception of the Epstein-Barr nuclear antigen (EBNA1), have epitopes that are presented on the B-cell surface in the context of common class I major histocompatibility complex (MHC) molecules, and are recognized by cytotoxic T lymphocytes. This high level of cytotoxic T-cell recognition and the ability of latently infected cells to shift between full latent gene expression with cell proliferation and an EBNA1-only type of latent infection that is immunologically privileged, enables latently infected cells to achieve a balanced state of long-term persistence in humans. This ability of EBV-infected cells to establish a balanced state of persistence in normal humans raised the possibility that cells infected with EBV recombinants could be used for genetic reconstitution, in vivo (Robertson, E. S. et al., *Proc. Natl. Acad. Sci. USA* 93:11334–11340 (1996)). The ability of superinfection raised the possibility that cells infected with EBV recombinants could be used in gene therapy for EBV-associated cancers (Paillard, F., *Human Gene Therapy* 9:1119–1120 (1998)).

Some B-cell lymphomas are EBV positive, especially AIDS-related brain lymphomas, with 100% of malignant cells being EBV positive. Although the role of EBV in the carcinogenesis of lymphomas is still not clear, EBV is certainly not the only factor. Because EBV is able to superinfect EBV-positive B lymphoma cells, an EBV vector carrying a suicide gene could be used to infect and kill the tumor cells. A recombinant EBV vector derived from the P3HR1 strain is an ideal choice because it does not have the EBNA2 gene that is essential for transformation of normal lymphocytes.

There are three difficulties in creating a recombinant EBV as an in vivo gene expression vector. First, the EBV genome is too large to be manipulated as a plasmid for DNA recombination in vitro. Generally, recombinant EBV is generated by homologous recombination. A positive selection marker, such as a gene that encodes an enzyme that inactivates a toxic drug, can be introduced into the EBV genome anywhere. A neomycin resistance gene was introduced into the EBV's thymidine kinase gene locus (Shimizu, N. et al., *J. Virol.* 70:7260–7263 (1996)) and a prokaryotic replicon, F factor, was inserted into the BamHI I fragment of the EBV genome (Delecluse, H. -J. et al.,*Proc. Natl. Acad. Sci. USA* 95:8245–8250 (1998)). The later approach allows the generation of viral mutants in *E. coli.*

Second, in order to allow for long-term persistence in vivo, the recombinant virus should preserve all the characteristics and functions of the wild-type EBV. That is, the viral vector must be able to complete its full life cycle in EBV's natural host, B lymphocytes.

Finally, the recombinant virus must be purified and reproduced to a reasonable titer in a cell line that is EBV-negative and supports EBV's productive cycle. It has been previously reported that EBV-negative Akata lymphoma cells and 293 cells could serve this purpose (Shimizu, N. et al., *J. Virol.* 70:7260–7263 (1996); Delecluse, H. -J. et al., *Proc. Natl. Acad. Sci. USA* 95:8245–8250(1998)).

One of the main objectives of gene therapy is to achieve stable, efficient, and persistent genetic modification of target cells. This means that their progeny, or themselves in the case of non-dividing cells, should retain and express the newly introduced genetic material until the end of their lifespan, ideally in a regulated manner. This principle is equally valid when transgenes are introduced to correct genetic deficiencies or for treatment of non-hereditary diseases. The viral vector systems discussed above can achieve retention of the transgene through different mechanisms. For example, retrovirus and AAV vectors can integrate genes into the genome of infected cells, while EBV-derived vectors are maintained by episomal replication.

A comparison of the different viral-based gene delivery systems is summarized below:

| Comparison of virus-based gene delivery systems | | | | | |
|---|---|---|---|---|---|
| Vector | Integration | Long-term expression | Transgene limit (kb) | Immunogenicity | Risk |
| Retrovirus | + | – | 8.5 | – | + |
| AV | – | – | 10 | +/– | – |
| AAV | + | – | 4.5 | – | – |
| HSV | – | – | 150 | + | – |
| mini EBV | – | – | 150 | – | – |
| recombinant EBV | – | + | 15 | – | +/– |

Clearly, there is a need in the art for additional and more efficient EBV-based viral vector systems that are capable of stably delivering and persistently expressing a transgene in B-lymphocytes, in vitro or in vivo. Such a vector would be useful for gene therapy of genetic diseases and deficiencies, as well as diseases such as congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma, and nasopharyngeal carcinoma.

SUMMARY OF THE INVENTION

The purpose of this invention was to find a convenient site in the EBV genome for recombining foreign genes in order to create a non-defective EBV vector that was capable of long-term persistence and expression of foreign genes in B lymphocytes in vivo. This vector would be useful for genetic reconstitution or for the treatment of B-cell lymphomas in humans.

The inventors have surprisingly found that the EBV major internal repeat region (IR1) is an effective site for recombination and expression of foreign genes, without adversely effecting EBV's latent and lytic life cycles.

The EBV major internal repeat (IR1) region consists of multiple copies of the BamHI "W" fragment (3072 bp each), which contains the Wp EBNA promoter and multiple exons for expression of EBNA-LP (Speck,S. H.et al., *Proc Natl Acad Sci USA* 83:9298–9302 (1986)). The EBNA-LP protein can be expressed from any exon and is essential for latent EBNA expression. The nucleotide sequence of IR1 has been determined (Cheung, A., et al., *J. Virol.* 44:286–294 (1982)).

Since its function was known and the BamHI W copy number can be quite variable, the inventors hypothesized that the EBV IR1 site might be a conducive region for accommodating foreign genes, so long as there was no influence on latent EBNA-LP expression. It was theorized that it would be much easier for a transgene to recombine into one of the multiple targets, than into a single target sequence. Insertion of a foreign gene in the middle area of a 3072 bp W fragment makes it easy for PCR assay to find the targeted recombinant virus.

In order to study the expression of foreign genes from IR1 and the potential effect on EBV-induced B-cell immortalization, latent gene expression, and lytic function, the inventors introduced the enhanced green fluorescent protein (EGFP) gene and a hygromycin phosphotransferase cDNA, controlled by a CMV promoter, into IR1 by homologous recombination in B95-8 cells. Hygromycin-resistant clones were screened by PCR for targeted recombination. The recombinant virus was confirmed by Southern blot analysis. The B95-8 cells containing recombinant virus spontaneously produced both recombinant and wild-type viruses. Pure recombinant virus infected peripheral blood lymphocytes (PBL) or 293 cell clones were selected after infection with the mixed virus preparation from B95-8 cells. Pure recombinant virus preparation can then be obtained from these cells by activation with anti-human IgG, TPA+ butyrate or by transfection of BZLF1 gene expressing plasmid. The strategy is shown in FIG. 9.

Southern blot analysis suggested that the insertion of EGFP was in the 7th of 8 BamHI W fragments in IR1. The recombinant EBV, designated EBwgh, was purified in peripheral blood B lymphocytes, 293 cells, and Akata(–) cells. In EBwgh transformed PBLs, Wp transcription and EBNA-LP expression were confirmed by RT-PCR and Western blot analyses, and long-term, high level GFP expression was observed. This indicated that insertion and expression of a foreign gene in any copy of the W fragment has no influence on EBV latent gene expression. EBNA-LP can be expressed directly from downstream sequences of the transgene or spliced over the transgene from the upstream of the transgene, depending on the position of the transgene.

It was concluded that foreign genes can be effectively and persistently expressed from the IR1 region without adverse effect on EBV latent gene expression, and that IR1 is a convenient site for recombining foreign genes into EBV. This non-defective EBV vector thus may be used for gene delivery and persistent expression in B lymphocytes in vivo. The technique to create this EBV vector is simple, easy, and efficient.

Accordingly, the present invention relates to the development and characterization of a gene delivery system based on an EBV vector having a transgene inserted in the EBV IR1 region. In a preferred embodiment, the transgene is inserted in any copy of the EBV IR1 W fragment, provided EBNA-LP expression is not adversely affected.

An exciting property of the vector system of the present invention is the ability of the vector to target B-lymphocytes, and due to a non-integrated episome, to persist in vivo for an extended time, once the vector is introduced. Accordingly, the present invention overcomes the disadvantages of the prior art.

Thus, the present invention provides viral vectors derived from Epstein-Barr Virus (EBV). In the most preferred embodiment, the EBV vector comprises at least one transgene of interest in the EBV major internal repeat region, for gene delivery and persistent expression in B-lymphocytes in vivo.

The transgene(s) may be a reporter or marker gene, and/or a therapeutic gene. Representative examples of suitable reporter genes include: β-galactosidase, green fluorescent protein (gfp), enhanced green fluorescent protein (egfp), galactokinase, alkaline phosphatase, chloramphenicol acetlytransferase, luciferase, and β-lactamase.

Representative examples of suitable selectable marker genes for mammalian cells include genes for blasticidin, histinidol D, hygromycin B, mycophenolic acid, neomycin, puromycin, zeocin, etc.

The therapeutic transgene sequence may be a gene sequence associated with diseases and disorders including, but not limited to genetic diseases and deficiencies, as well as diseases such as congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma, and nasopharyngeal carcinoma. Of course, other genetic elements may also be present in the EBV construct, such as additional regulatory, therapeutic, reporter, or marker genes.

The transgene may also be a bacterial artificial chromosome (BAC) backbone for further genetic modification of the EBV viral genome in E. coli.

The invention further provides a method for expressing a transgene in a B-lymphocyte cell population, in vitro or in vivo using the EBV vectors of the invention. Some exemplary in vivo applications for the gene delivery system of the invention include diseases such as genetic diseases and deficiencies, as well as diseases such as congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma, and nasopharyngeal carcinoma.

The invention also provides a method of treating diseases and disorders using the vectors of the invention. Non-limiting examples of the diseases and disorders that can be treated using the present vectors include, for example, the diseases mentioned above.

In another embodiment, the invention provides a method of selectively killing B-lymphocyte neoplasms using the vectors of the invention. The EBV vectors of the invention can be engineered to contain prodrug-activating genes or "suicide genes" in the EBV IR1 region.

It is to be understood that both the foregoing general description and the following detailed description are exemplary and explanatory and are intended to provide further explanation of the invention as claimed.

BRIEF DESCRIPTION OF THE FIGURES

FIG. 8A depicts B95-8/EBwgh with hygromycin selection; FIG. 8B depicts PBL/EBwgh without hygromycin selection; FIG. 8C depicts IB4 cells with hygromycin selection, superinfected with EBwgh from PBL/EBwgh.

FIG. 9 depicts the strategy for engineering and preparing EBwgh.

DETAILED DESCRIPTION OF THE PREFERRED EMBODIMENTS

Figure 1:
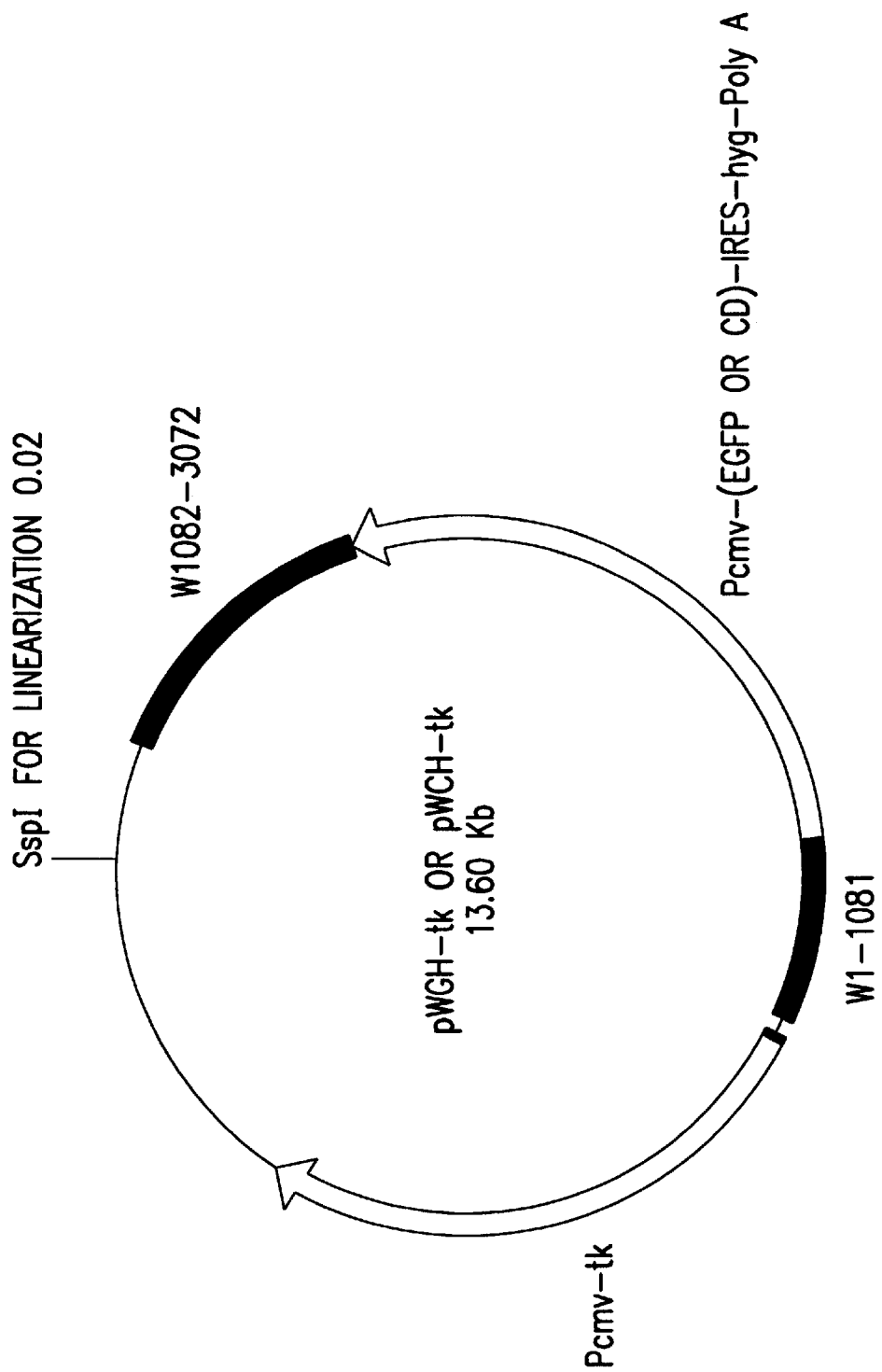
FIG. 1 depicts the plasmid construct pWGH-tk or pWCH-tk for homologous recombination in IR1. The plasmid size is 13.6 kb.

The present invention relates to the development and characterization of a gene delivery system based on an EBV vector having at least one transgene inserted in the EBV IR1 region. In a preferred embodiment, the transgene is inserted in any copy of the EBV IR1 W fragment so long as EBV's latent and lytic life cycles are not adversely affected.

The term "EBV," as used herein, is intended to include any EBV strain or isolate, or any EBV "relative," such as other members of the gamma herpes virus family, which are B-lymphotropic to humans and other mammals. That is, the term "EBV" should not be limited to a particular strain or isolate of the virus.

The EBV IR1 region consists of multiple copies of the BamHI "W" fragment (3072 bp each) of the EBV genome, which contains the Wp EBNA promoter and multiple exons for expression of EBNA-LP (Speck,S. H.et al., Proc Natl Acad Sci USA 83:9298–9302 (1986)). The EBNA-LP protein can be expressed from any exon and is essential for latent EBNAs expression. The nucleotide sequence of IR1 has been determined (Cheung, A., et al.,J. Virol. 44:286–294 (1982)).

Since its function was known and the BamHI W copy number can be quite variable, the inventors hypothesized that the EBV IR1 site might be a conducive region for accommodating foreign genes, so long as there was no influence on latent EBNA-LP expression. It was theorized that it would be much easier for a transgene to recombine into one of the multiple targets, than into a single target sequence. Insertion of a foreign gene in the middle area of a 3072 bp W fragment makes it easy for PCR assay to find the targeted recombinant virus.

The above definition of the EBV IR1 region as "multiple copies of the BamHI W fragment of the EBV genome," is a definition suited for the EBV B95-8 strain, and may not accurately cover all EBV strains, isolates, and EBV relatives in the gamma herpes virus family (since every one may not be cut by BamHI). Thus, the term "EBV IR1 region," as used herein, is intended to include the repeated sequences in the IR1 region of any EBV strain or isolate, as well as the corresponding region in EBV "relatives," such as other members of the gamma herpes virus family, that divide the genome into short and long largely unique sequence domains (US and UL).

An exciting property of the EBV vector system of the present invention, is the ability of the vector to target B-lymphocytes, and due to a non-integrated episome, to persist in vivo, for an extended time, once the vector is introduced. Accordingly, the present invention overcomes the disadvantages of the prior art.

Thus, the present invention provides viral vectors derived from Epstein-Barr Virus (EBV). In the most preferred embodiment, the EBV vector comprises at least one transgene of interest in the EBV major internal repeat region, for gene delivery and persistent expression in B-lymphocytes in vivo.

The inserted transgene in the EBV major internal repeat region may be a reporter or marker gene, and/or a therapeutic gene.

The term "transgene," as used herein, is intended to refer to a gene sequence, and is a nucleic acid molecule. Such transgenes, or gene sequences, may be derived form a variety of sources including DNA, cDNA, synthetic DNA, RNA, or combinations thereof. Such transgenes may comprise genomic DNA, which may or may not include naturally occurring intros. Moreover, such genomic DNA may be obtained in association with promoter regions or poly A sequences. The transgenes of the present invention are preferably genomic DNA or cDNA. Genomic DNA or cDNA may be obtained by means well known in the art. One or more transgenes may be present in the EBV vector constructs of the invention.

The transgene may be any gene sequence whose expression produces a gene product that is to be expressed in a cell. The gene product may affect the physiology of the host cell, and/or may be therapeutic. Examples of gene sequences that can be used as therapeutic transgenes, include, but are not limited to, a gene sequence associated with genetic diseases and deficiencies, as well as disorders such as such as congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma, and nasopharyngeal carcinoma.

For gene-deficiency disorders, such as adenosine deaminase deficiency, or deficiencies in clotting factor VIII or IX, gene therapy with the EBV vectors of the invention could be used to bring a normal gene into affected tissues for replacement therapy, as well as to create animal models for the disease using, e.g., antisense mutations.

Thus, the invention also provides for an EBV vector wherein the inserted transgene sequence is a gene sequence associated with diseases and disorders. Non-limiting examples of such diseases and disorders are listed above.

The term "transgene cassette," as used herein, is intended to refer to a transgene operably linked to a promoter or other regulatory sequence sufficient to direct transcription of the transgene. Suitable promoters include, for example, a human CMV IEI promoter or an SV40 promoter, or any eukaryotic promoters well known to those skilled in the art. The transgene cassette may also optionally have termination signals, processing signals, or introns. It is of course possible to use as a transgene a gene sequence that already possesses a promoter, initiation sequence, introns, processing sequence or termination sequence in the transgene cassette.

Alternatively to using one or more therapeutic transgenes, or in addition to using one or more therapeutic transgenes in the vectors of the invention, the vectors may also contain one or more non-therapeutic transgenes, such as reporter genes or selectable marker genes.

A "reporter gene," as used herein, is any gene sequence which, when expressed, results in the production of a protein whose presence or activity can be easily monitored. Examples of suitable reporter genes can include the gene for a-galactosidase, green fluorescent protein (GFP), enhanced green fluorescent protein (egfp), galactokinase, alkaline phosphatase, chloramphenicol acetyltransferase, luciferase, and a-lactamase.

A "selectable marker gene," as used herein, is any gene sequence capable of expressing a protein whose presence permits selective propagation of a cell which contains it. Examples of selectable marker genes for mammalian cells include genes for blasticidin, histinidol D, hygromycin B, mycophenolic acid, neomycin, puromycin, zeocin, etc.

Of course, other genetic elements may also be present in the vector, such as additional regulatory, therapeutic, reporter, or marker genes. That is, the EBV vector can bear multiple transgenes in the IR1 region. Genes particularly suited for inclusion include: 1) marker genes; 2) therapeutic genes, genes that can be used to replace a deficiency state (such as adenosine deaminase, clotting factor VIII or IX), or suicide genes that activate a prodrug (i.e., HSV-tk, bacterial cytosine deaminase; cytochrome P450); 3) regulatory elements or genes, for example encoding drug/hormone inducible systems, such as the tetracycline transactivator and silencing proteins (Freundlieb, S., et al., *Methods Enzymol.* 283:159–173 (1997)) or dimerizing system (Amara, J. F., et al., *Proc. Natl. Acad. Sci. USA* 94:10618–10623 (1997)); and 4) genes for proteins which can reduce the immunogenicity of the vector (Hahne, M., et al., *Science* 274:1363–1366 (1996)), which may be especially important for cancer gene therapy applications.

Finally, the transgene may also be a bacterial artificial chromosome (BAC) backbone for further genetic modification of the EBV viral genome in *E. coli*.

As used herein, the term "BAC" is intended to mean a cloning and sequencing vector derived from a bacterial chromosome into which a fragment of 100,000 bases or more of DNA can be inserted. BACs are based on the single-copy plasmid F factor of *E. coli,* and have been demonstrated previously to stably maintain human genomic DNA of greater than 300 kb, and genomes of large DNA viruses, including those of baculovirus and murine cytomegalovirus (Shizuya, H., et al., *Proc. Natl. Acad. Sci. USA* 89:8794–8797 (1992); Luckow, V. A., et al., *J. Virol.* 67:4566–4579 (1993); Messerle, M., et al., *Proc. Natl. Acad. Sci. USA* 94:14759–14763 (1997)).

As used herein, the term "BAC backbone" is intended to mean the minimal region required for F-factor replication and maintenance (O'Connor, M., et al., *Science* 244:1307–1312 (1989)). The backbone of the BAC contains at least one origin of replication needed for replication in *E. coli*.

One of the major problems in gene therapy, as mentioned before in the background section, is the retention of the genetic elements that are introduced by the various vectors. By "retention" of the genetic elements is intended the continued presence in transduced cells for more than four generations in dividing cells, and more than one month in non-dividing cells.

In a particularly preferred embodiment of the invention, the EBV vector is called EBwgh. The strategy for engineering this vector is depicted in FIG. 9 and discussed in Example 1.

The term "host cell" or "target cell" is intended to refer to any cell that can be infected with the EBV vectors of the present invention. Mammalian B-lymphocyte cells are particularly preferred target cells. Mammalian B-lymphocyte cells from mammals within the order Primates (e.g., humans, apes, monkeys, baboons, lemurs, etc . . . ) are most preferred. By "B-lymphocyte" is intended those lymphocyte cells that develop from pluripotential hematopoietic stem cells and are responsible for the production of immunoglobulins. The B-lymphocyte cell can be normal or abnormal (such as B-lymphoma cells).

The term "operably linked" is intended to describe a linkage between a gene sequence and a promoter or other regulatory or processing sequence such that the transcription of the gene sequence is capable of being directed by an operably linked promoter sequence, the translation of the gene sequence is capable of being directed by an operably linked translational regulatory sequence and the post-translational processing of the gene sequence is capable of being directed by an operably linked processing sequence.

The invention further provides a method for expressing a transgene in a B-lymphocyte cell population, in vitro or in vivo, using the EBV vectors of the invention. Some exemplary in vivo applications for the gene delivery system of the invention include treatment of genetic diseases and deficiency states, as well as congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma and nasopharyngeal carcinoma.

Accordingly, the invention also provides a method of treating diseases and disorders using the vectors of the invention. Non-limiting examples of the diseases and disorders that can be treated using the present vectors include: genetic diseases and deficiency states, congenital lymphoid immunodeficiencies, such as adenosine deaminase deficiency, hematological disorders, such as hemophilia, B-cell lymphomas, such as AIDS-related brain lymphomas, and other EBV-associated cancers, such as Burkitt's lymphoma (BL), Hodgkin's lymphoma and nasopharyngeal carcinoma.

In yet another embodiment, the invention provides a method of selectively killing neoplastic cells using the EBV vectors of the invention. Gene therapy can be used to introduce a gene into the tumor cells that expresses a protein which is toxic or can trigger a toxic effect against tumor cells. Genes for transfer into the neoplastic cells by the EBV vectors are selected from those which target host cell usually by expression of a gene product in the host neoplastic cells. "Gene product" broadly refers to proteins encoded by the particular gene. For the purposes of the invention, gene product also includes transcription products of the gene, particularly for use as antisense RNA. Genes are selected whose gene products serve to identify host cells, slow down or temporarily stimulate host cell growth in order to render the host cell more sensitive to chemotherapeutic agents and/or whose products target the host cell for cell death. Cell death can be accomplished by contacting the host cells, containing the gene product, with a subsequent treatment, either physical or chemical treatment. Alternatively, the gene products themselves may serve to kill the host cells or slow down cell growth.

In this embodiment, the host cells targeted by the EBV vectors of the invention are abnormal B-lymphocyte cells, such as B-lymphoma cells, or malignant cells, such as nasopharyngeal carcinoma cells (an EBV-associated cancer), into which the EBV vector infects and expresses the desired gene product.

Useful gene products comprise: tumor suppressor genes, which encode transcription factors which suppress cell growth, such as the Rb gene for retinoblastoma or the p53 gene in colon cancer (Huang, H. J., et al., *Science* 242: 1563–1566 (1988); Baker, S. J., et al., *Science* 249: 912–915 (1990)); toxic proteins that are released by cells, such as a fusion protein comprising a toxin coupled to EGF ligand (Heimbrook, D. C., et al., *Proc. Natl. Acad. Sci. USA* 87: 4697–4701 (1990)); products which themselves trigger apoptosis or are capable of selective cell killing or growth inhibition, such as anti-sense nucleic acid for essential cell proteins, and replication proteins which serve to render the host cells incapable of further cell growth and division (Rosenberg,U. B., et al., *Nature* 313: 703–706 (1985); Preiss, A, et al., *Nature* 313:27–32 (1985); McGarry, T. J., et al., *Proc. Natl. Acad. Sci USA* 83: 399–403(1986)); prodrug activating genes such as HSV thymidine kinase (tk) (Kramm,C. M., et al., *Brain Pathology* 5:345–381 (1995); Ezzeddine, Z. D., et al., *New Biol.* 3:608–614(1991)), cytosine deaminase (CD) (Mullen, C. A., et al., *Proc. Natl. Acad. Sci. USA* 89: 33–37 (1992); Huber, B. E., et al., *Cancer Res.* 53:4619–4626 (1993); Mullen, C. A., et al., *Cancer Res.* 54:1503–1506 (1994)), or cytochrome P450 (Chen, L. and Waxman, D. J., *Cancer Research* 55:581–589 (1995); Wei, M. X., et al., *Hum. Gene Ther.* 5:969–978 (1994)); and genes encoding proteins that block angiogenesis (O'Reilly, M., et al., *Cell* 88:277–285 (1997)).

For example, an EBV vector which incorporates the HSV-1 thymidine kinase gene offers a conditional killing mechanism for EBV-associated cancers, such as nasopharyngeal carcinoma (NPC). The thymidine kinase enzyme can convert certain nucleoside analogues, such as, acyclovir, ganciclovir, and FIAU. These drugs are converted to nucleotide-like precursors and incorporated into the DNA of the replicating cells, thus disrupting the integrity of the genome and ultimately leading to cell death. (See, Boviatsis, E. J., et al., *Cancer Res.* 54:5745–5751 (1994). Thus, the EBV vector administered in combination with a less toxic drug could be highly effective treatment for EBV-associated cancers.

The EBV vector can also incorporate the bacterial cytosine deaminase (CD) gene, which confers lethal sensitivity to 5-fluorocytosine (5-FC) (Huber et al., *Cancer Res.* 53:4619–4626(1993); Mullen et al., *Cancer Res.* 54:1503–1506 (1994)). Since the CD/5-FC system has a bystander effect in B-lymphocytes, it would be a preferred system for targeting B-lymphoma cells.

In addition, the EBV vector can also incorporate the gene for cytochrome P450. The cytochrome P450 gene offers a conditional killing mechanism independent of the cell cycle of the tumor cell. This gene is used to sensitize neoplastic cells to the cytotoxic effects of a chemotherapeutic agent that is activated by one or more cytochrome P450 genes. The term "cytochrome P450 gene," as used herein, means a mammalian cytochrome P450 gene such as, P450, 2B1, P450 2B6, P450 2A6, P450 2C8, P450 2C9, P450 2C11, or P4503A4. Each of these genes has been linked to activation of the anticancer drugs cyclophosphamide, oxazaphophorine or ifosphamide (Clarke, L., et al., *Cancer Res.* 49:2344–2350 (1989); Chang, T K H, et al., *Cancer Res.* 53:5629–5637 (1993); Weber, G. F., et al., *Biochemical Pharmacology* 45:1685–1694 (1993), and the cDNA sequences of these genes have also been published (Nelson, D. R., et al., *DNA and Cell Biology* 12:1–51 (1993) and references cited therein; Yamano, S., et al., *Biochem.* 29:1322–1329 (1990); Yamano,S., et al., *Biochem.* 28:7340–7348 (1989). Persons of ordinary skill in the art will be able to utilize the method and vectors of the present invention with numerous other anticancer drugs that are activated by members of the cytochrome P450 family of enzymes that are homologous to the aforementioned cytochromes. In one embodiment for selectively killing neoplastic cells, the cytochrome P450 2B1 gene can be utilized to sensitize lymphomas or EBV-associated cancers to the cytotoxic effects of cyclophosphamide (CPA).

In another embodiment, more than one prodrug-activating gene may be inserted in the EBV vector system of the invention, in order to achieve synergistic effects. For example, the HSV-tk gene coupled with the bacterial cytosine deaminase(CD) gene may be used together, as may the HSV-tk gene with a cytochrome P450 gene. Other combinations of prodrug-activating genes, known to those skilled in the art, may also be used in the vectors and methods of the invention. An overview on prodrug-activating genes (also called "suicide genes") for cancer gene therapy may be found in Aghi, M., et al., *The Journal of Gene Medicine* 2:148–164 (2000) and Freeman, S. M., et al., *Semin. Oncol.* 23:31–45 (1996).

The EBV vector can be administered to a primate directly by multiple routes, including, e.g., direct injection into a tumor mass, through the blood vessels, via cerebrospinal fluid, or via an infected packaging cell. Most preferably, however, for the establishment of long-term balanced status, the EBV vector should be administered to lymphocytes ex vivo; that is, a blood sample of the primate host is obtained, the B-lymphocytes are isolated from the blood, the B-lymphocytes are infected in vitro with the EBV vector of the invention, the transduced cells are then reintroduced back to the host (i.e., in vivo). This technique is well-known to those skilled in the art.

The gene product may also encode a chemical or protein which renders the host cells radiosensitive and thus more susceptible to killing by radiation. Thus, upon subsequent subjection to radiation, the host cells are selectively killed.

Thus, the following types of cancers and tumors can be treated using the EBV vectors of the invention: B-cell lymphomas and EBV-associated cancers, such as Hodgkins lymphoma, Burkitt's lymphoma (BL), and nasopharyngeal carcinoma (NPC).

Thus, the invention further provides a method for expressing a transgene in a B-lymphocyte cell, which comprises:
(a) introducing an EBV vector of the invention into the cell; and
(b) permitting the vector to express the transgene in the B-lymphocyte cell.

The invention also provides a method of selectively killing neoplastic cells from an EBV-associated neoplasm, comprising:
(a) infecting said neoplastic cells with an EBV vector expressing thymidine kinase, wherein expression of the thymidine kinase gene product renders said tumor cells sensitive to ganciclovir or acyclovir;
(b) administering an effective amount of ganciclovir or acyclovir; and
(c) selectively killing said neoplastic cells.

The invention also provides a method of selectively killing neoplastic cells from a B-cell lymphoma, comprising:
(a) infecting said neoplastic cells with an EBV vector expressing bacterial cytosine deaminase (CD), wherein expression of the CD gene product renders said tumor cells sensitive to 5-fluorocytosine;
(b) administering an effective amount of 5-fluorocytosine; and
(c) selectively killing said neoplastic cells.

The invention also provides the foregoing methods, wherein the EBV vector additionally expresses a second prodrug-activating gene, in addition to HSV-tk or CD.

The invention further provides for a method of selectively killing neoplastic cells comprising:
(a) infecting said neoplastic cells with an EBV vector expressing cytochrome P450, wherein expression of the cytochrome P450 gene product renders said tumor cells sensitive to a chemotherapeutic agent;
(b) administering to the patient an effective amount of a chemotherapeutic agent that is activated by the cytochrome P450 enzyme; and
(c) selectively killing said neoplastic cells. In a preferred embodiment, the chemotherapeutic agent is cyclophosphamide or ifosfamide. Also, in a preferred embodiment, the neoplastic cells are B-cell lymphomas or EBV-associated neoplasms.

The invention also provides the foregoing method, wherein the EBV vector expresses a second prodrug-activating gene, in addition to cytochrome P450.

The present invention is further illustrated by the following examples. These examples are provided to aid in the understanding of the invention and are not construed as a limitation thereof.

EXAMPLE 1

Construction and Characterization of the EBV Vector

Materials and Methods

Plasmid construction. The plasmid used for introduction of the EGFP and hygromycin phosphotransferase cDNAs by homologous recombination into EBV's IR1 was constructed as follows: an EBV BamHI W fragment(3072 bp) was subcloned into pBSKII (Stratagene, La Jolla, Calif.) to generate plasmid pBSW. EGFP cDNA was PCR amplified and subcloned into the Nsi I site of pIREShyg (Clontech, Palo Alto, Calif.) to generate pEGFPiresHyg. The Pcmv-EGFPiresHyg expression cassette was excised as an Nru I-Xho I fragment from pEGFPiresHyg, was blunt-ended, and then subcloned into the SnaB I site of W fragment in pBSW to generate pWGH. A PcmvHSVtk expression unit was excised from pCMVtk as a Hind III fragment, blunt-ended and then subcloned into the blunt-ended Not I site of pWGH to generate the final plasmid pWGH-tk (FIG. 1).

Another plasmid, pWCH-tk, was also generated with the same strategy, but using the cytosine deaminase (CD) gene instead of the EGFP gene. The resulting plasmids were linearized with Ssp I and electroporated into B95-8 cells (ATCC, Manassas, Va.) or P3HR1 cells. B-95-8 cells are derived from an EBV-positive marmoset B-cell line. P3HR1 cells are derived from an EBV-positive human Burkitt's lymphoma cell line.

Cell culture. All cells were cultured at 37° C. in an atmosphere containing 5% carbon dioxide in RPMI 1640, supplemented with 10% fetal calf serum. Medium was changed twice weekly.

Figure 2:
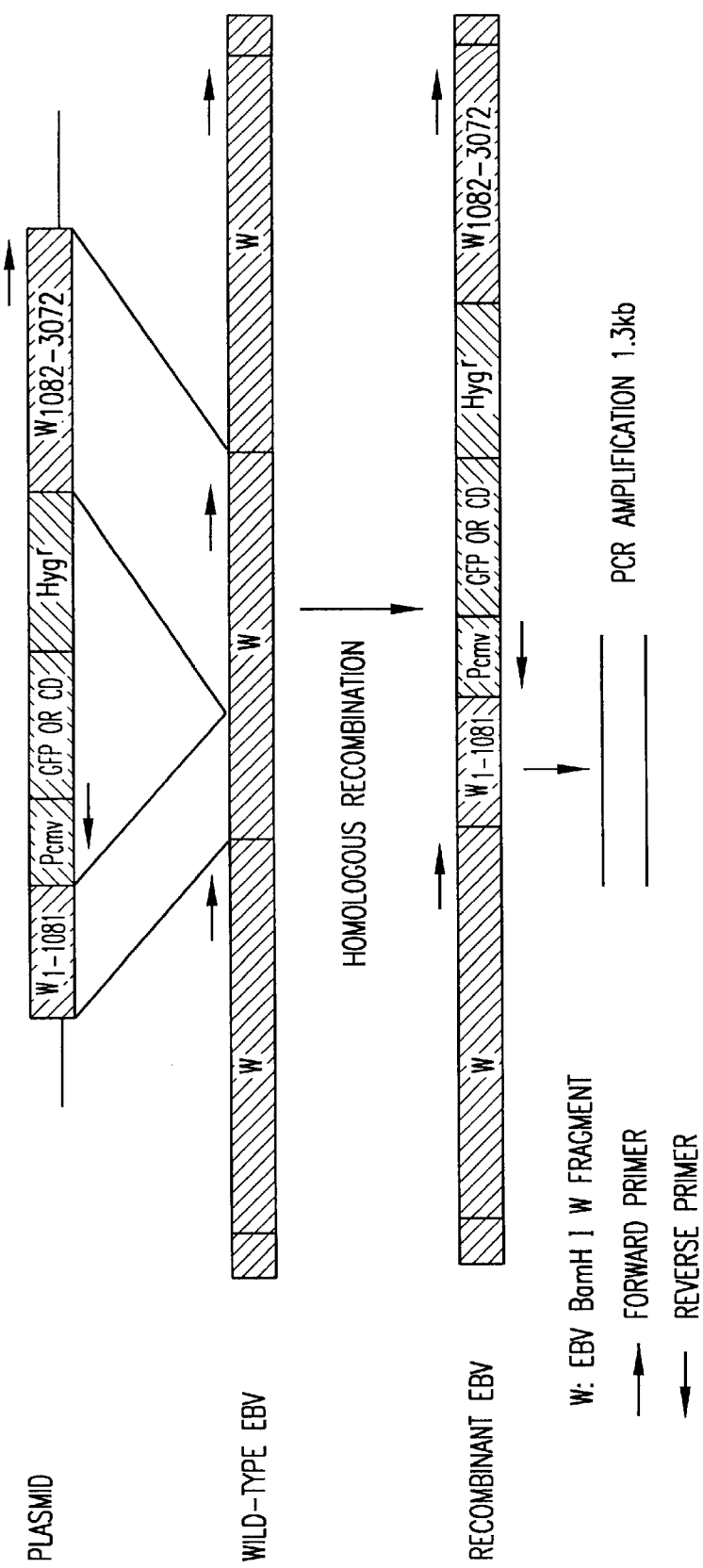
FIG. 2 is a schematic depicting homologous recombination in IR1 and PCR screening of recombinant EBV.

Engineering of recombinant EBVs. 10–20 ug linearized pWGH-tk or pWCH-tk was electroporated into $5 \times 10^6$ cells in 0.4 ml electroporation buffer/cuvette with Gene Pulser (Bio-Rad, Hercules, Calif.) at 220V, 960 uF. Electroporated cells were added to 6× volume of medium and cultured for two days. Then, the cells were transferred at 100 ul medium/well into 96-well plates with hygromycin at 200 ug/ml for positive selection. 10–14 days after electroporation, 100 ul medium containing ganciclovir (GCV) (Roche Laboratories Inc., Nutley, N.J.) was added into the culture at a final concentration of 1 ug/ml for negative selection. Total DNAs, including viral DNA, were extracted from cell clones that had survived 4–5 weeks after electroporation and after positive and negative selection. These DNAs were screened for recombinant EBV by PCR. The forward primer was designed to match the W fragment at site 2818–2847 and the reverse primer was designed to match the CMV promoter. A 1.3 kb fragment can be amplified only from homologously recombinant EBV. Amplification was not observed from either linearized plasmid or wild-type EBV (FIG. 2).

Southern blot analysis. Viral DNAs were isolated after lysis of cells with SDS/proteinase K, repeated phenol-chloroform extraction and ethanol precipitation. DNA was digested with Hind III and Nsi I, separated by agarose electrophoresis, and transferred to a nylon membrane (Amersham Corp., Arlington, Ill.). The EBV BamHI W fragment was then used as a hybridization probe. Labeling of the probe and hybridization were performed using the ECL chemiluminescence system(Amersham).

Purification of EBwgh by infection of Akata(−) cells. $1 \times 10^6$ Akata(−) cells of 2A8 subclones were infected with 1 ml of 1:40 diluted supernatant from B95-8/EBwgh cells, at 37° C., 5% $CO_2$ for 2 hours. One day after infection, the cells were put into a 1×96-well plate under selection with hygromycin at 200 ug/ml for four weeks.

Purification of EBwgh by transformation of peripheral blood lymphocytes (PBL). $2\times10^7$ PBL cells in 1 ml of medium and 2 ml of supernatant from B95-8/EBwgh culture were incubated at 37° C., 5% $CO_2$ for 2 hours, then put into a 1×96-well plate. Three weeks later, hygromycin was added at 200 ug/ml.

RT-PCR assay for W promoter transcription. Total RNA was extracted from the cells using the RNAeasy kit (Qiagene,Valencia, Calif.). RT-PCR was performed with $W_0$ primer and Y primer according to the EBNA-LP cDNA sequence (Sample, J., et al., *Proc. Natl. Acad. Sci USA* 83:5096–5100 (1986) using the SuperScript kit (Life Technologies, Gaithersburg, Md.) according to manufacturer's protocol. PCR products were separated by agarose gel electrophoresis.

Western blot analysis. The cell pellet was dissolved with lysis/loading buffer at 1000 cells/ul. 30 ul of samples were separated by 10% SDS-PAGE gel electrophoresis, and transferred to a nitrocellulose membrane. Mouse anti-EBNA-LP was used as the first antibody and signals were detected with the ECL chemiluminescence system (Amersham), according to the manufacturer's manual.

Activation of EBV lytic cycle in infected PBL/EBwgh. $1\times10^6$ cells/ml were treated with 20 ng/ml of TPA and 1 mM butyrate or 0.5% rabbit anti-human IgG (Dako, Corp.), or $1\times10^7$ cells were electroporated with 40 ug EBV BZLF1 gene expression plasmid pSVNZ and then 4 ml media was added. After a 5-day culture, the supernatant was harvested and filtered through a 0.45 u filter.

Superinfection of Raji cells or IB4 cells with EBwgh. $2.5\times10^6$ Raji cells or $5\times10^6$ IB4 cells were incubated with 1 ml or 2 ml supernatant from activated PBL/EBwgh culture at 37° C., 5% $CO_2$ for 2 hours and then were put into a 96-well plate. Two days after infection, hygromycin was added at 200 ug/ml as selection for 3 weeks. Raji cells are derived from EBV-positive human Burkitt lymphoma lines. IB4 cells are derived from EBV-positive fetal lymphoblastoid cell lines, with the EBV genome integrated.

Observation of GFP expression. Cells were observed under a fluorescent microscope.

Results

Engineering of recombinant EBV's. Five survival clones were obtained from 5 electroporations with pWGH-tk and 11 survival clones were obtained from 11 electroporations with pWCH-tk after positive and negative selection. One out of 5 clones was found with recombinant EBwgh by PCR, and 4 out of 11 clones were found with recombinant EBwch by PCR. For EPwgh (the P3HR1strain with pWGH-tk electroporated), 4 out of 20 GFP-positive survival clones were found by PCR. See, Table 1.

TABLE 1

Result of Engineering of Recombinant EBVs

| Cells | Plasmid | No. of Electroporations | No. Survival Clones | No. With Rec. PCR Amplification |
|---|---|---|---|---|
| B95-8 | pWGH-tk | 5 | 5 | 1 |
| B95-8 | pWCH-tk | 11 | 11 | 4 |
| P3HR1 | pWGH-tk | 24 | 289* | 4 (out of 20 screened)* |

*Only 20 survival clones were GFP-positive and were screened.

Figure 3:
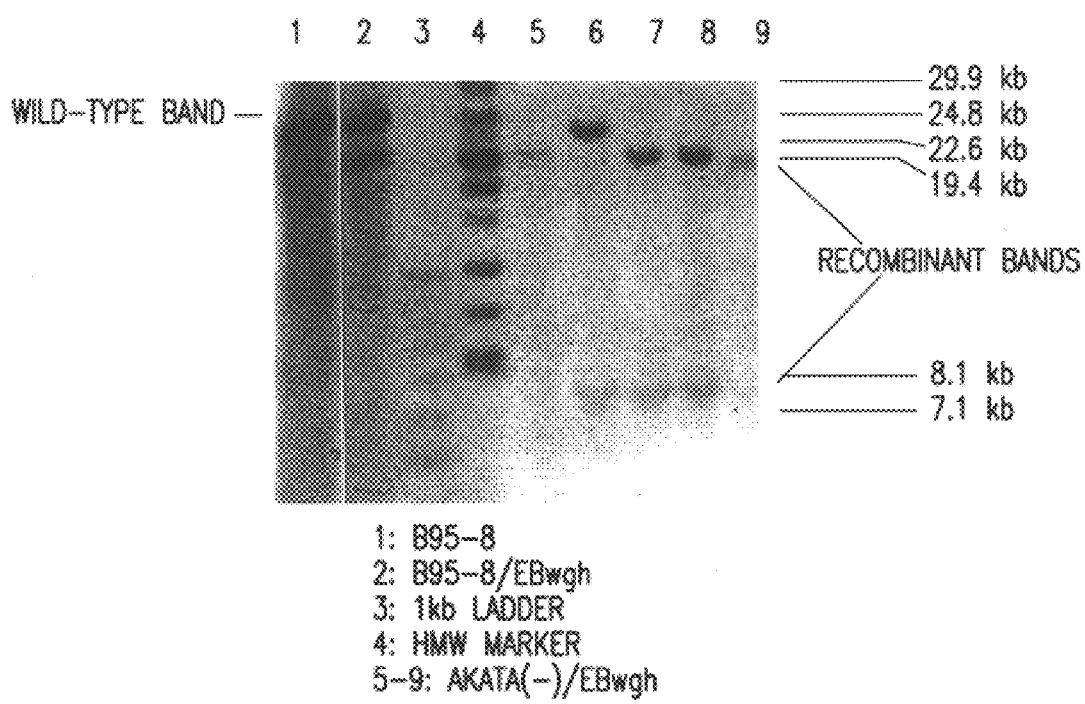
FIG. 3 is a Southern blot of EBwgh. Viral DNA was digested with Hind III and Nsi I and probed with W fragment.
Figure 4:
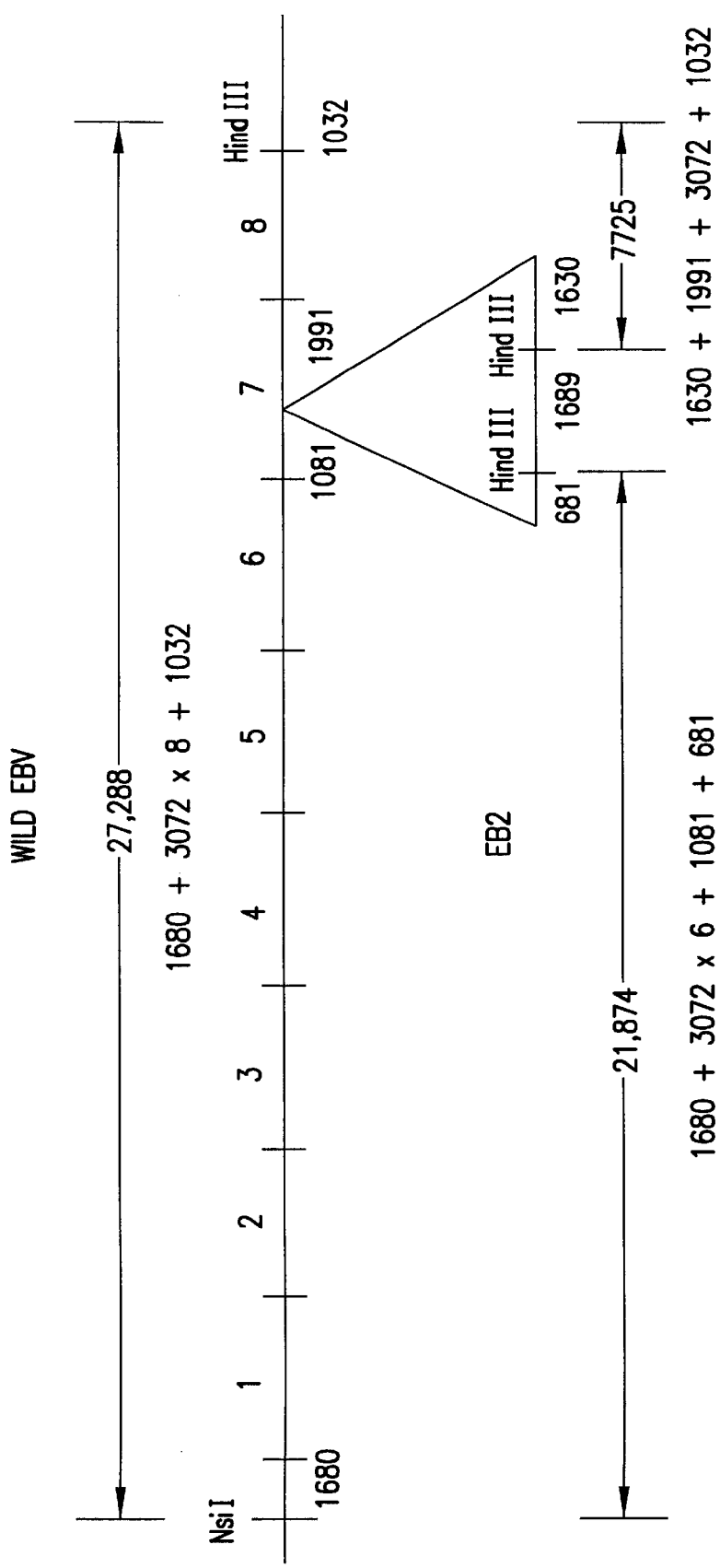
FIG. 4 indicates the strategy for the Southern analysis of EBwgh and the result of localization calculation of EBwgh.

Localization of the foreign gene inserted in the IR1 region of EBwgh. The insertion was localized in the 7th of 8 BamH I W fragment in IR1 by Southern hybridization analysis (FIGS. 3 and 4).

Purification of EBwgh by infection of Akata(−) cells. Thirty clones with hygromycin resistance and GFP(+) were obtained. Five (5) clones analyzed by Southern blot were all infected only by Ebwgh (FIG. 3).

Figure 5:
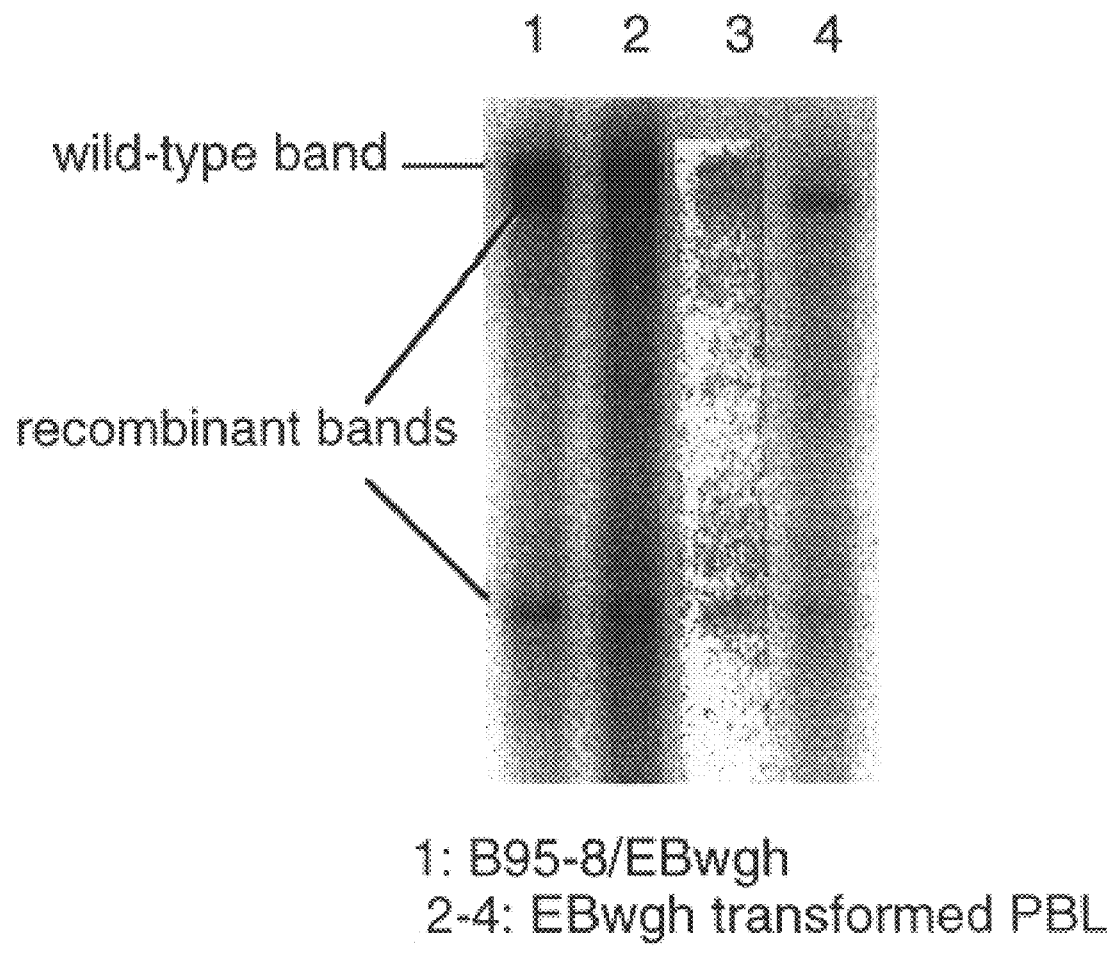
FIG. 5 depicts a Southern blot analyses of EBwgh transformed peripheral blood lymphocytes (PBL). Viral DNA was digested with Hind III and Nsi I and probed with W fragment.

Purification of EBwgh by transformation of PBL. 20 clones with GFP expression were initially selected from $2\times10^7$ PBL cells infected with 2 ml of supernatant from B95-8/EBwgh culture. Four of these clones remained stable. One out of 3 of the clones analyzed by Southern blot had only two recombinant signal bands, but no wild-type EBV signal band (FIG. 5, lane 4); this indicated that this clone was infected only by EBwgh.

Figure 6:
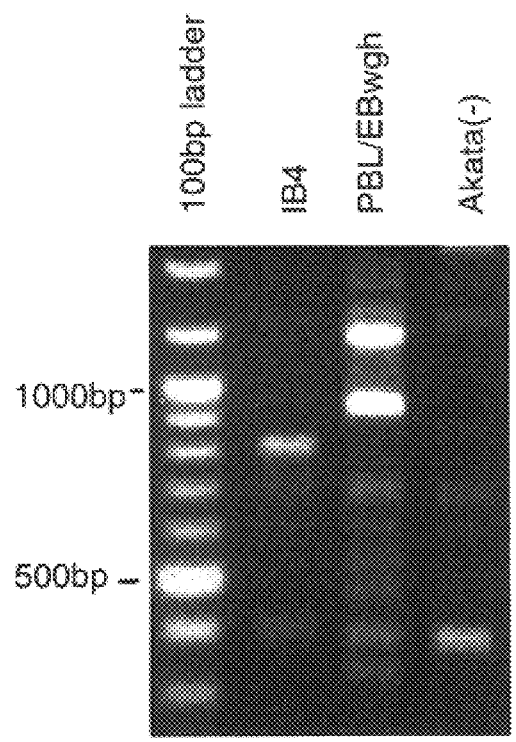
FIG. 6 depicts RT-PCR for W promoter transcription.
Figure 7:
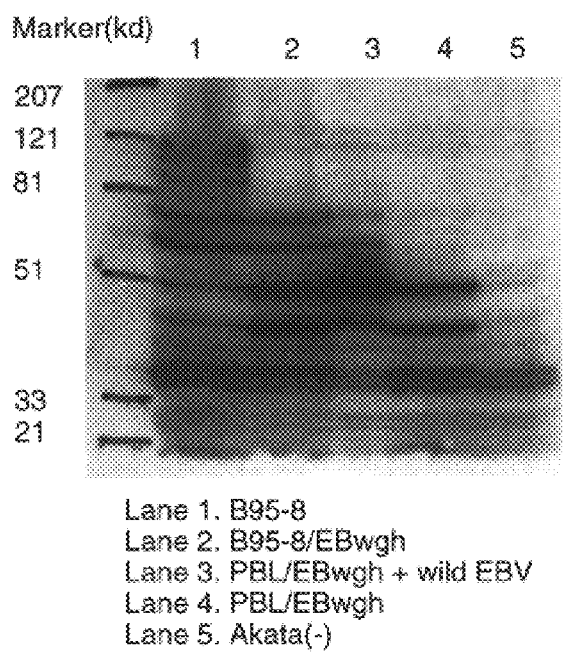
FIG. 7 depicts a Western blot analysis of EBNA-LP expression in PBL/EBwgh cells.

PBL/EBwgh's transcription from Wp and expression of EBNA-LP. There were 2 signal bands in the gel electrophoresis of RT-PCR assay for W promoter transcription (FIG. 6) and 3 major signal bands on the Western blot analysis for EBNA-LP expression from PBL/EBwgh. The greater number of bands with Western blot was most likely due to the greater sensitivity of Western blot compared with RT-PCR. This compared to a greater number of bands from the parental B95-8 cells (FIG. 7).

Activation of lytic cycle of EBwgh in PBL cells. Some survival clones, under hygromycin selection, appeared in the 96-well plate from Raji cells and IB4 cells superinfected with supernatant from different activation treatment of PBL/EBwgh cell cultures. The most effective activation treatment was anti-IgG (Table 2).

TABLE 2

Raji cells and IB4 cells superinfection assay for EBwgh production

| | No. of GFP positive | |
|---|---|---|
| Treatment of PBL/EBwgh | Raji cells (well) | IB4 cells (well) |
| no | 3 | 1 |
| TPA + butyrate | 39 | 37 |
| pSVNZ electroporation | 80 | 89 |
| anti-IgG | 91 | 96 |

Figure 8A:
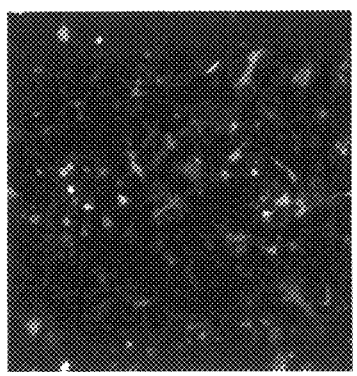
FIGS. 8A, 8B, and 8C depict GFP expression of cells containing EBwgh.
Figure 8B:
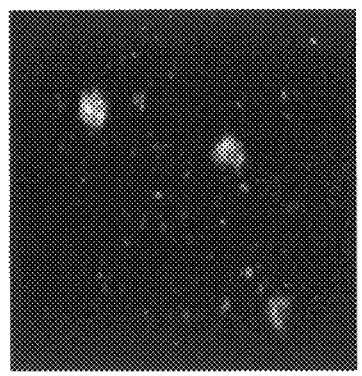
Figure 8C:
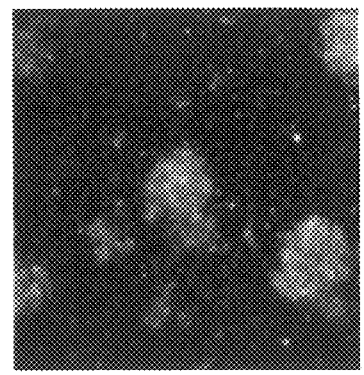

GFP expression. Under culture, without hygromycin selection for three months, 100% of PBL/EBwgh cells remained GFP positive (FIG. 8), while B95-8/EBwgh and EBwgh+wild EBV co-transformed PBL cells had 1 month half life-time of GFP-positive cell loss.

Discussion

The strategy for engineering, purifying, and reproducing the recombinant EBV of the invention is represented in FIG. 9. In this Example, high efficiency recombination in IR1 was achieved. 1 EBwgh and 4 EBwch were isolated from 16 electroporations and by 16 PCR reactions. Four EBwgh (out of 20 GFP-positive survival clones that were screened) were isolated from 24 electroporations and by 20 PCR reactions. Since IR1 consists of repeated W fragment, it was much easier for a transgene to recombine into one of the multiple targets than into a single target sequence. Insertion of a foreign gene in the ⅓ site of a 3072 bp W fragment leaves about 1 kb size at one side, which is long enough for efficient homologous recombination yet also short enough for PCR screening to find the targeted recombinant virus.

Another factor that contributed to the high engineering efficiency was the performance of the HSV-tk/GCV negative selection system. Since homologous recombination occurred between the electroporated two partial W fragments flanking the foreign genes, the HSV-tk expression unit was out of this homologous recombination region and would be lost. Otherwise, when the plasmid was randomly integrated into the cellular and/or viral genomes, the HSV-tk expression unit might be included and, as a result, produce sensitivity to ganciclovir. This would allow negative selection against the positive selection resistant clones with randomly integrated plasmid.

Another advantage of using IR1 for accommodating foreign genes is that it can increase the transgene packaging capacity, since the BamHI W copy number can be quite variable, from 4–12, this can be a packaging constraint in the virus size.

IR1 contains the Wp promoter and multiple exons for EBNA-LP expression. This protein can be expressed from any exon (that makes different EBNA-LP sizes and multiple bands can be seen in FIG. 7) and is essential for latent EBNAs expression. The exemplified recombinant EBV has the transgene inserted in its 7th of 8 W copies in IR1 and its EBNA-LP expression was spliced over the insertion from upstream. This indicates that insertion of a foreign gene in any copy of the W fragment has no influence on the EBNA-LP expression. EBNA-LP can be either expressed directly from downstream of the transgene or spliced from upstream over the transgene, depending on the position of the transgene insertion. During EBV's productive cycle (lytic cycle), there are over 100 genes expressed. The insertion of a transgene in IR1 has no influence on the lytic cycle either, because the recombinant EBV virus of the invention can be produced in EBV's natural host cell—B lymphocytes. This ability may be required for EBV's long-term persistence in vivo.

Persistent ex vivo GFP expression in PBL/EBwgh cells was observed without selection for 3 months, compared to a 30-day half-life of persistence with non-transforming mini-EBV (Banerjee, S., el al., Nature Med.1:1303–1308 (December1995)).

EBV-positive Burkitt's lymphoma (BL) cells—i.e. Raji, P3HR1, and Akata cells, could be superinfected by EBwgh. Although EBwch, containing a CD gene, was not further characterized, it is expected to be useful for gene therapy for the EBV-associated cancers (Paillard, F., *Human Gene Therapy* 9:1119–1120 (1998)). The P3HR1 strain EBV recombinant virus is a preferred choice because it does not have the EBNA2 gene, which is essential for the transformation of normal B-lymphocytes.

In this Example, EBwgh could be easily purified with PBL, Akata (−) cells and 293 cells. The remaining issue was how to produce the purified recombinant virus from those cells. The use of Akata(−) cells was not successful here. Even the parental Akata(+) cells, under optimized condition, were not able to produce an EBV titer as high as the B95-8 cells when undergoing the lytic cycle spontaneously. The 293 cells produced a comparable titer with PBL (data not shown). Thus, the data showed that the transformed PBLs, as well as 293 cells, were an appropriate producer for EBwgh.

From this Example, it can be concluded that foreign genes can be effectively expressed from IR1 without adverse effect on EBV latent gene expression and that IR1 may be a convenient site for recombining foreign genes into EBV as a gene delivery vector for B-lymphocytes. The technique for introduction of foreign gene(s) into the IR1 region is simple and efficient. Another advantage of using IR1 for accommodating foreign transgenes is that it may increase the transgene packaging capacity, since the BamHI W copy number can be quite variable, from 4–12. This can be a packaging constraint in the virus size.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A viral vector, comprising:
   an Epstein-Barr virus (EBV) genome, wherein a heterologous nucleotide sequence operatively linked to a promoter is inserted into the major internal repeat region of said EBV genome, and wherein said vector can target B-lymphocyte cells and express said heterologous nucleotide sequence therein.

2. The viral vector of claim 1, wherein said heterologous nucleotide sequence is inserted in any copy of the EBV IR1 W fragment.

3. The viral vector of claim 2, wherein the B-lymphocyte cells are mammalian cells from the order Primates.

4. A host cell transformed with the viral vector of claim 2.

* * * * *